United States Patent [19]

Weber-Unger

[11] 4,164,228

[45] Aug. 14, 1979

[54] PAD FOR NURSING BRASSIERES

[76] Inventor: Georg Weber-Unger, Am Brand 2, 8201 Nussdorf/Inn, Fed. Rep. of Germany

[21] Appl. No.: 846,558

[22] Filed: Oct. 28, 1977

[30] Foreign Application Priority Data

Nov. 5, 1976 [DE] Fed. Rep. of Germany ... 7635406[U]

[51] Int. Cl.² ............................................... A41C 3/00
[52] U.S. Cl. .................................... 128/461; 128/150
[58] Field of Search ............... 128/461, 460, 438, 463, 128/150, 280, 481; 2/104

[56] References Cited

U.S. PATENT DOCUMENTS

| 2,258,209 | 10/1941 | Jorio | 128/461 |
| 2,495,307 | 1/1950 | Abramson | 128/150 |

FOREIGN PATENT DOCUMENTS 836238  4/1952  Fed. Rep. of Germany ........... 128/150

Primary Examiner—Werner H. Schroeder
Assistant Examiner—Doris L. Troutman
Attorney, Agent, or Firm—Parmelee, Johnson, Bollinger & Bramblett

[57] ABSTRACT

An absorbent pad for nursing brassieres with a cap-shaped part proportioned to the shape of the breast and with an absorbing apron attached to the cap-shaped part which apron increases the absorption volume of the pad as a whole.

5 Claims, 7 Drawing Figures

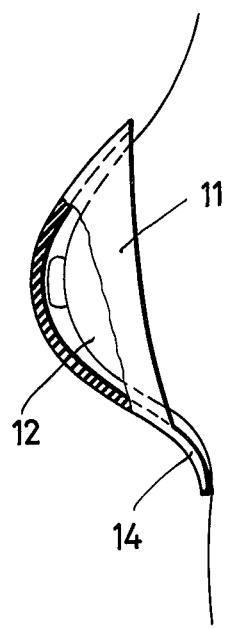
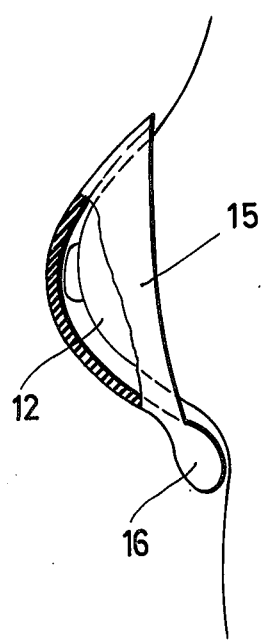
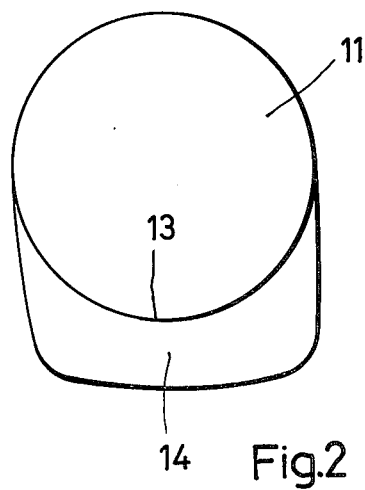
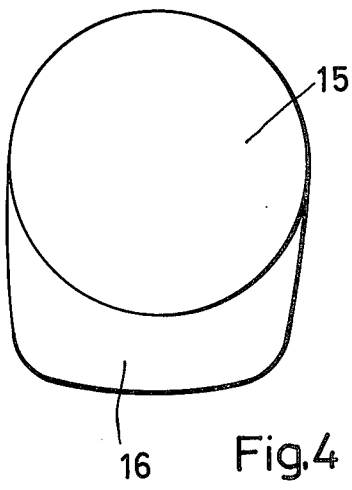

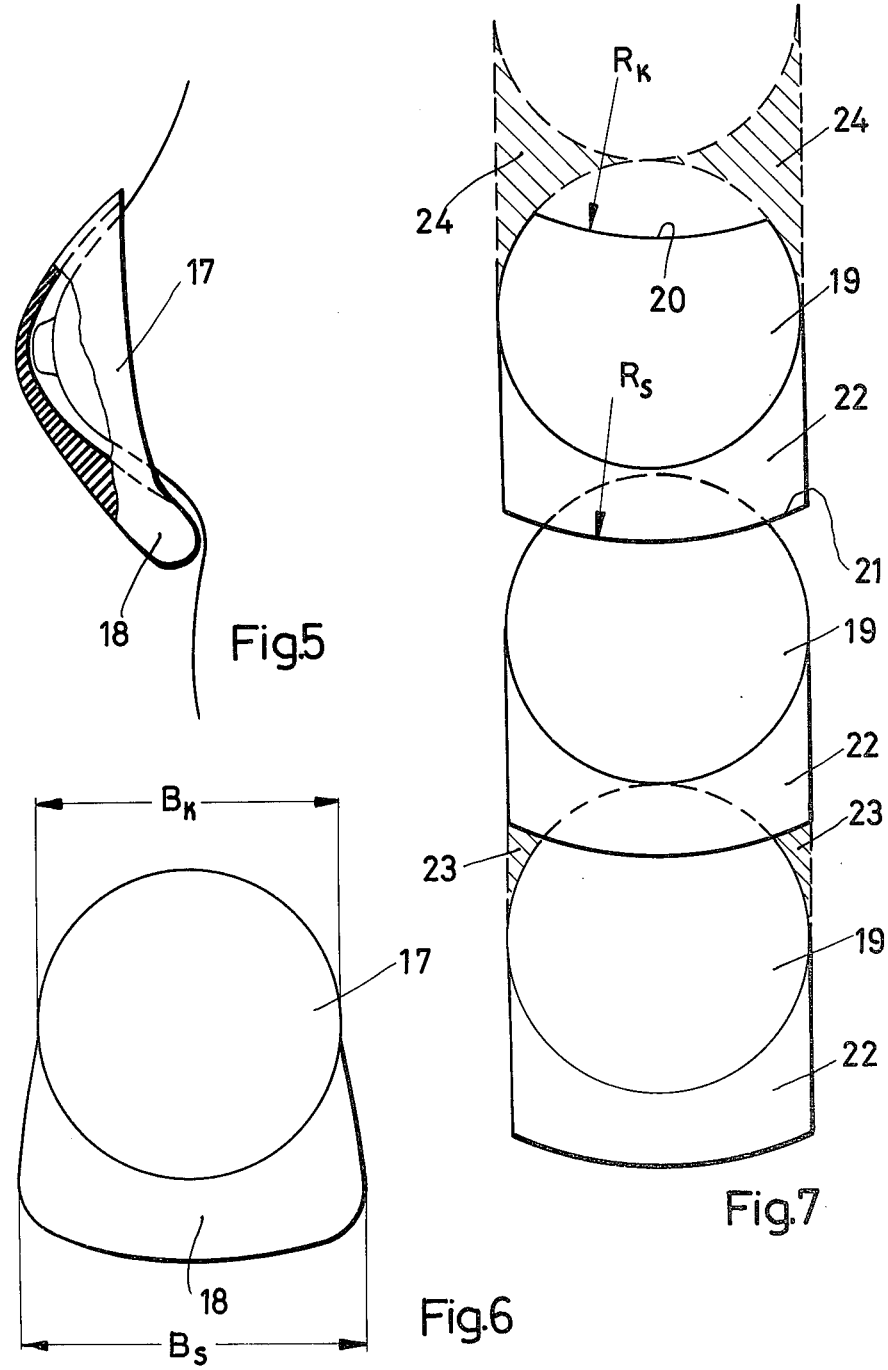

PAD FOR NURSING BRASSIERES

The invention concerns a pad for nursing brassieres with a cap-shaped part proportioned to the shape of the breast, consisting of absorbent material to catch rests of the mother's milk.

Pads of the above mentioned type with a circular circumference are known. These caps are not fully satisfactory as their absorption volume is comparatively small.

Also, pads with a greater absorption volume are known, which are formed by rectangular compresses. The disadvantage of this second type of pads consists therein that they do not adjust too well to the contours of the body.

It is the object of the invention to provide a pad which combines the advantages of the two known types of pads, without possessing their disadvantages. This object is solved therein that an absorbing apron, which increases the absorption volume of the pad, is attached to the cap-shaped part of the pads described before.

The pad according to the invention takes into consideration that the milk coming from the glands of the breast flows downwardly in accordance with the force of gravity, and that a great absorption reservoir here is advantageous and desirable.

For the further increase of the absorption volume it is advisable to strengthen the pad in the region of the absorbing apron. Especially advantageous is a solution wherein the thickness of the material is steadily increased from the center of the cap-shaped part to the absorbing apron.

In a preferred embodiment the cap-shaped part shows a sickle-shaped edge portion at its end facing away from the absorbing apron, the radius of curvature of the edge portion being essentially equal to the radius of curvature of the lower edge of the absorbing apron. Such a design does not only offer functional advantages, it also allows a more economic production of the pads in question.

The invention is described in more detail by way of the enclosed drawing:

FIG. 1 shows, partly sectional, the side view of a first pad,

FIG. 2 shows the plan view of the pad,

FIG. 3 shows, partly sectional, the side view of a second pad,

FIG. 4 shows the plan view of the pad according to FIG. 3,

FIG. 5 shows, partly sectional, the side view of a third pad,

FIG. 6 shows the plan view of the pad according to FIG. 5 and

FIG. 7 shows the plan view of several pads made of a strip of material.

The pad shown in FIGS. 1 and 2 has a cap-shaped part 11, the shape of which is adapted to the shape of the breast 12. An absorbing apron increasing the absorption volume of the pad is attached at the lower end 13 of the cap-shaped part 11. The thickness of the material of the cap-shaped part 11 and of the absorbing apron 14 is essentially constant in the first embodiment.

In the second embodiment in FIGS. 3 and 4 the pad consists of a cap-shaped part 15 and an absorbing apron 16. The absorbing apron 16 is in this case strengthened as against the cap-shaped part 15.

While in the embodiments described at first the thickness of the material of the pad is constant at least in the cap-shaped part, it increases already in the cap-shaped part 17 in the embodiment according to FIGS. 5 and 6, to reach its thickest part in the region of the absorbing apron 18. For further increasing the absorption volume of the absorbing aprong 18 its width $B_S$ is greater then the width $B_K$ of the cap-shaped part 17.

In a preferred embodiment, whereby one proceeds from a strip of an absorbing material for its production, the cap-shaped part 19 has a sickle-shaped edge portion 20, the radius of curvature $R_K$ of which is essentially equal to the radius of curvature of the lower edge 21 of an absorbing apron 22. The loss of material in the production of such pads is extremely small, as the hatched zones 23 show. In the production of known pads with circular circumference the loss of material corresponds to the zones 24, indicated in the upper part of FIG. 7. In the way described the loss of material is not only reduced, instead absorbent material is also moved from a region where it is not needed to a region where it is urgently required.

I claim:

1. An absorbing pad for nursing brassieres, said absorbing pad being formed of absorbent material, said absorbing pad including a cap-shaped portion proportioned to fit the contour of the breast and being so positioned in said nursing brassier that it is adjacent to the breast of the wearer, said absorbing pad further including an extension affixed to the lower periphery of said cap-shaped portion and extending downwardly therefrom, characterized therein that said extension forms an absorbing apron being positioned adjacent to the body of the wearer, said absorbing apron being formed of such material so that it generally conforms to the contour of the body of the wearer and is capable of absorbing discharged fluids, whereby the absorbing area of said nursing brassier is increased by the presence of said absorbing apron.

2. An absorbing pad as claimed in claim 1, wherein said absorbing apron is thicker than said absorbing pad for increasing the volume of fluids which can be absorbed.

3. An absorbing pad as claimed in claim 1, wherein said absorbing pad progressively increases in thickness in a direction from the center of said cap-shaped portion towards said absorbing apron.

4. An absorbing pad as claimed in claim 1, in which the width ($B_S$) of said absorbing apron is greater than the width ($B_K$) of said cap-shaped portion.

5. An absorbing pad as claimed in claim 1, wherein said cap-shaped portion has a sickle-shaped edge portion at its end which faces away from said absorbing apron, the radius of curvature ($R_K$) of said edge portion being essentially equal to the radius of curvature ($R_S$) of the lower edge of said absorbing apron.

* * * * *